(12) United States Patent
Horst

(10) Patent No.: US 8,308,944 B2
(45) Date of Patent: Nov. 13, 2012

(54) SYSTEM AND METHOD FOR TREATING WASTEWATER VIA PHOTOTACTIC HETEROTROPHIC MICROORGANISM GROWTH

(75) Inventor: Geoff Horst, Howell, MI (US)

(73) Assignee: Algal Scientific Corporation, Plymouth, MI (US)

( * ) Notice: Subject to any disclaimer, the term of this patent is extended or adjusted under 35 U.S.C. 154(b) by 390 days.

(21) Appl. No.: 12/727,738

(22) Filed: Mar. 19, 2010

(65) Prior Publication Data

US 2010/0237009 A1 Sep. 23, 2010

Related U.S. Application Data

(60) Provisional application No. 61/161,787, filed on Mar. 20, 2009.

(51) Int. Cl.
*C02F 3/32* (2006.01)

(52) U.S. Cl. ........ 210/602; 210/611; 210/620; 210/205; 210/221.2; 210/259

(58) Field of Classification Search .................. 210/602, 210/610, 611, 620, 630, 748.1, 205, 206, 210/221.2, 252, 259

See application file for complete search history.

(56) References Cited

U.S. PATENT DOCUMENTS

| | | | |
|---|---|---|---|
| 3,316,674 A | 5/1967 | Shirota et al. | |
| 3,444,647 A | 5/1969 | Takahashi et al. | |
| 3,768,200 A | 10/1973 | Klock | |
| 3,780,471 A | 12/1973 | Ort et al. | |
| 3,882,635 A | 5/1975 | Mitsugi et al. | |
| 3,954,615 A | 5/1976 | Shelef | |
| 3,955,318 A | 5/1976 | Hulls et al. | |

(Continued)

FOREIGN PATENT DOCUMENTS

CN 2338338 9/1999

(Continued)

OTHER PUBLICATIONS

A Photo-Bioreactor Using Algal Phototaxis for Solids-Liquid Separation; Toshiyuki Nakajima and Masahiro Takahashi; Advanced Wastewater Treatment Division, Water Quality Control Department, Public Works Research Institute, Ministry of Construction, Tusukuba, Japan vol. 25, No. 10, pp. 1243-1247 (1991).

(Continued)

*Primary Examiner* — Fred Prince
(74) *Attorney, Agent, or Firm* — Fraser Clemens Martin & Miller LLC; Jacob M. Ward

(57) ABSTRACT

A wastewater treatment method includes the steps of supplying a wastewater influent having nutrients for a population of phototactic heterotrophic microorganisms to an aerated bioreactor. At least a portion of the nutrients is converted into the phototactic heterotrophic microorganism population. The wastewater influent and the phototactic heterotrophic microorganism population together form a bioreactor effluent that is transferred to a light clarifier. The bioreactor effluent is concentrated in the light clarifier to form a low-solids effluent and a high-solids effluent. The concentration is performed by inducing the population of phototactic heterotrophic microorganisms to phototactically self concentrate through exposure to a light having at least one of an intensity and a wavelength sufficient to cause the phototactic heterotrophic microorganism population to migrate away from a source of the light. The high-solids effluent is then dewatered to form a concentrated biomass paste. The low-solids effluent is further processed to form a treated water stream.

20 Claims, 4 Drawing Sheets

U.S. PATENT DOCUMENTS

| | | | |
|---|---|---|---|
| 4,005,546 A | 2/1977 | Oswald | |
| 4,209,388 A | 6/1980 | Defraites | |
| 4,267,038 A | 5/1981 | Thompson | |
| 4,348,285 A | 9/1982 | Schluter et al. | |
| 4,966,713 A | 10/1990 | Burgin et al. | |
| 5,055,402 A | 10/1991 | McPherson et al. | |
| 5,071,462 A | 12/1991 | Kimura | |
| 5,084,386 A | 1/1992 | Tuse et al. | |
| 5,176,100 A | 1/1993 | Fujino | |
| 5,338,673 A | 8/1994 | Gudin et al. | |
| 5,385,832 A | 1/1995 | Tuse et al. | |
| 5,407,576 A | 4/1995 | Dolderer et al. | |
| 5,462,666 A | 10/1995 | Kimmel | |
| 5,476,787 A | 12/1995 | Yokoyama et al. | |
| 5,647,983 A | 7/1997 | Limcaco | |
| 5,744,041 A | 4/1998 | Grove | |
| 5,958,241 A | 9/1999 | DeBenedetto et al. | |
| 6,027,900 A | 2/2000 | Kyle et al. | |
| 6,254,775 B1 | 7/2001 | McElvaney | |
| 6,416,993 B1 | 7/2002 | Wexler et al. | |
| 6,465,240 B1 | 10/2002 | Wexler et al. | |
| 6,837,991 B1 | 1/2005 | Norris | |
| 6,896,804 B2 | 5/2005 | Haerther et al. | |
| 7,438,813 B1 | 10/2008 | Pedros et al. | |
| 7,578,933 B1 | 8/2009 | Selman | |
| 2001/0044143 A1 | 11/2001 | Herman et al. | |
| 2002/0034817 A1 | 3/2002 | Bakken et al. | |
| 2002/0079270 A1 | 6/2002 | Konstantinov et al. | |
| 2002/0130076 A1 | 9/2002 | Merritt | |
| 2002/0153303 A1 | 10/2002 | Oswald et al. | |
| 2003/0034299 A1 | 2/2003 | Moghe et al. | |
| 2003/0209489 A1 | 11/2003 | Haerther et al. | |
| 2003/0217826 A1 | 11/2003 | Brosch et al. | |
| 2003/0228684 A1 | 12/2003 | Harper et al. | |
| 2004/0026317 A1 | 2/2004 | Hubenthal et al. | |
| 2005/0061737 A1 | 3/2005 | Linden et al. | |
| 2005/0064577 A1 | 3/2005 | Berzin | |
| 2005/0287561 A1 | 12/2005 | Wolfson et al. | |
| 2006/0096918 A1 | 5/2006 | Semmens | |
| 2007/0048848 A1 | 3/2007 | Sears | |
| 2007/0108123 A1 | 5/2007 | Lee et al. | |
| 2008/0011659 A1 | 1/2008 | Hsiao et al. | |
| 2008/0096267 A1 | 4/2008 | Howard et al. | |
| 2008/0118964 A1 | 5/2008 | Huntley et al. | |
| 2008/0120749 A1 | 5/2008 | Melis et al. | |
| 2008/0124756 A1 | 5/2008 | Dillon | |
| 2008/0135474 A1 | 6/2008 | Limcaco | |
| 2008/0155888 A1 | 7/2008 | Vick et al. | |
| 2008/0160591 A1 | 7/2008 | Willson et al. | |
| 2009/0004715 A1 | 1/2009 | Trimbur et al. | |
| 2009/0028775 A1 | 1/2009 | O'Rear | |
| 2009/0029427 A1 | 1/2009 | Miller | |
| 2009/0029446 A1 | 1/2009 | O'Rear | |
| 2009/0047722 A1 | 2/2009 | Chen | |
| 2009/0134091 A1 | 5/2009 | Stephens et al. | |
| 2009/0137025 A1 | 5/2009 | Stephens et al. | |
| 2009/0145844 A1* | 6/2009 | Chang et al. | 210/605 |
| 2009/0148931 A1 | 6/2009 | Wilkerson et al. | |
| 2009/0162919 A1 | 6/2009 | Weissman et al. | |
| 2009/0200230 A1 | 8/2009 | Abreu et al. | |
| 2009/0249685 A1 | 10/2009 | Flowers et al. | |
| 2009/0305942 A1 | 12/2009 | Brooks et al. | |
| 2009/0317857 A1 | 12/2009 | Kilian et al. | |
| 2009/0325253 A1 | 12/2009 | Ascon et al. | |
| 2009/0325270 A1 | 12/2009 | Fleischer et al. | |
| 2010/0021968 A1 | 1/2010 | Sommerfeld et al. | |
| 2010/0022393 A1 | 1/2010 | Vick | |
| 2010/0035321 A1 | 2/2010 | Wilkerson et al. | |
| 2011/0159581 A1* | 6/2011 | Zhang et al. | 435/292.1 |

FOREIGN PATENT DOCUMENTS

| | | |
|---|---|---|
| CN | 1958485 | 5/2007 |
| CN | 101104539 A | 1/2008 |
| CN | 201002986 Y | 1/2008 |
| CN | 201027184 Y | 2/2008 |
| CN | 101139224 A | 3/2008 |
| CN | 101280273 A | 10/2008 |
| CN | 101306879 A | 11/2008 |
| CN | 101330156 A | 12/2008 |
| CN | 101343090 A | 1/2009 |
| CN | 101367575 A | 2/2009 |
| CN | 101386799 A | 3/2009 |
| CN | 101418316 A | 4/2009 |
| DE | 19649244 | 5/1998 |
| EP | 1801197 | 6/2007 |
| EP | 1972602 A | 9/2008 |
| EP | 1995304 A | 11/2008 |
| FR | 2874006 A | 2/2006 |
| GB | 200915377 A | 10/2009 |
| JP | 10174997 | 6/1998 |
| JP | 2001170671 | 6/2001 |
| JP | 2002315568 | 10/2002 |
| JP | 2004357670 | 12/2004 |
| JP | 2005185925 | 7/2005 |
| JP | 2008093650 A | 4/2008 |
| JP | 2008272721 A | 11/2008 |
| JP | 2009022887 A | 2/2009 |
| KR | 20000020150 | 4/2000 |
| KR | 20070061504 | 6/2007 |
| KR | 100784509 B | 12/2007 |
| RU | 2312072 C | 12/2007 |
| WO | WO 8303333 | 10/1983 |
| WO | WO 9851814 | 11/1998 |
| WO | WO 0039032 | 7/2000 |
| WO | WO 2004101447 | 11/2004 |
| WO | WO 2006042371 A | 4/2006 |
| WO | WO 2007010068 A | 1/2007 |
| WO | WO 2008136793 A | 11/2008 |
| WO | WO 2008151373 A | 12/2008 |
| WO | WO 2009000534 A | 12/2008 |
| WO | WO 2009002772 A | 12/2008 |
| WO | WO 2009066231 A | 5/2009 |
| WO | WO 2009043763 A | 9/2009 |
| WO | WO 2009125897 A | 10/2009 |
| WO | WO 2009149260 A | 12/2009 |

OTHER PUBLICATIONS

Purification and Reclamation of Farm and Urban Wastes by *Euglena gracilis*: Photosynthetic Capacity, Effect of pH, Temperature, Acetate and Whey; E.R. Waygood, A. Hussain, H.R. Godavari, Y.C. Tai & S.S. Badour; Department of Botany, University of Manitoba, Winnipeg, Manitoba, Canada; Environmental Pollution (Series A) 23 (1980) 179-215.

Polarotaxis, gravitaxis and vertical phototaxis in the green flagellate, *Euglena gracilis*; D.P. Hader; Fachbereich Biologie-Botanik, Lahnberge, D-3550 Marburg, Federal Republic of Germany; Arch Microbiol (1987) 147: 179-183.

The Effect of Photon Irradiance on the Behavioral Ecology and Potential Niche Separation of Freshwater Phytoplanktonic Flagellates; Mark R. Clegg, Stephen C. Maberly & Roger I. Jones; Centre for Ecology and Hydrology Windermere, Ambleside Cumbria; Dept of Biological Sciences, Lancaster; J. Phycol. 39, 650-662 (2003).

Discovery of signaling effect of UV-B/C light in the extended UV-A/blue-type action spectra for step-down and step-up photophobic responses in the unicellular flagellate alga *Euglena gracilis*; Matsunaga, Hori, Takahashi, Kubota, Watanabe, Okamoto, Masuda & Sugai; Institute of Biological Sciences, etc.; Toyama University, Toyama; Protoplasma (1998) 201: 45-52.

* cited by examiner

SYSTEM AND METHOD FOR TREATING WASTEWATER VIA PHOTOTACTIC HETEROTROPHIC MICROORGANISM GROWTH

CROSS-REFERENCE TO RELATED APPLICATIONS

This application claims the benefit of U.S. Provisional Patent Application No. 61/161,787, filed on Mar. 20, 2009. The entire disclosure of the above application is hereby incorporated herein by reference.

FIELD OF THE INVENTION

The present disclosure relates to a wastewater treatment system and method, and more particularly, to a wastewater treatment system and method of using a population of a heterotrophic microorganism.

BACKGROUND OF THE INVENTION

A state of the art bacterial-based wastewater treatment system and method 100 is shown in FIG. 1. The system and method 100 includes providing a waste source 102 such as a municipal sewer line. A wastewater stream 104 from the waste source 102 has an undesirable biological oxygen demand (BOD), and high nitrogen and phosphorus concentrations. This wastewater stream may also have other undesirable chemical compounds broadly classified as metals, neurotoxins, or endocrine disrupting compounds.

The wastewater stream 104 from the waste source 102 typically undergoes a primary treatment 106 where the wastewater stream 104 flows through large tanks, commonly called "primary clarifiers" or "primary sedimentation tanks". The primary treatment 106 may be preceded by a pre-treatment (not shown) where materials that can be easily collected from wastewater stream 104 are removed, for example, by screening before they reach the primary clarifiers. The purpose of the primary sedimentation stage is to produce both a generally homogeneous influent 108 capable of being treated biologically, and a primary clarifier sludge (not shown) that can be separately treated and processed. The primary clarifiers usually are equipped with mechanically driven scrapers that continually drive the collected sludge 110 towards a hopper in the base of the tank, from which the collected sludge 110 can be pumped to further sludge treatment stages. Grease and oil from the floating material can sometimes be recovered for saponification during the primary treatment 106.

The effluent 108 from the primary treatment 106 then becomes the influent 108 to secondary treatment step 112 that is designed to substantially degrade the biological content of the influent 108. In a particular embodiment, the influent 108 is treated by an activated sludge process that uses aerobic bacteria to biologically remove organic matter from the influent 108. Under aerobic conditions provided by an input of oxygen, typically by bubble aeration, the bacteria consume the organic matter while generating new biomass and carbon dioxide. During the activated sludge process, bacteria growth tends to form large aggregates or flocs. In a particular embodiment, these flocs can settle to the bottom of additional secondary clarifiers, where the flocs of bacteria become the activated sludge. This sludge can be pumped to further sludge treatment stages or pumped back into the aerobic treatment stage to aid in consuming more organic matter.

The influent 108 can then undergo a tertiary treatment 116 which is intended to remove some portion of the remaining nitrogen and phosphorus. A carbon source 118 such as a methanol stream 120 may be added during the tertiary treatment 116 to aid in the process of de-nitrification where ammonia is converted to nitrites, and the nitrates are ultimately converted to nitrogen gas. In a particular embodiment, chemical inputs such as aluminum sulfate or iron salts are added to bind with phosphorus and form flocs that settle out in gravity clarifiers.

Following the tertiary treatment 116 of the influent 108, a disinfection treatment 122 may be conducted to produce a treated effluent 124 for release to the environment 126 such as a river. The purpose of the disinfection treatment 122 is to substantially reduce the quantity of microorganisms such as the aerobic bacteria to be discharged back into the environment 126. The effectiveness of disinfection depends on the quality of the influent 108 being treated (e.g., cloudiness, pH, etc.), the type of disinfection being used, the disinfectant dosage (concentration and time), and other environmental variables.

Nutrient removal in conventional wastewater treatment processes such as the bacterial-based wastewater treatment system and method 100 described above is known to be inefficient. Removal of organic solids from the wastewater stream 104, for example, with chemical flocculants and centrifuges, is particularly problematic.

It is also known to use aquatic microorganisms such as algae in wastewater treatment. Particular systems and methods employing algae in wastewater treatment are described in U.S. Pat. No. 6,465,240 to Wexler et al. and U.S. Pat. No. 6,896,804 to Haerther et al., the entire disclosures of which are hereby incorporated herein by reference. Wexler et al. discloses a method for treating a waste stream by contacting the waste stream sequentially with a consortium of prokaryotic microorganisms, preferably purple non-sulfur bacteria, followed by a green algae, Chlorella. The consortium of prokaryotic microorganisms assimilates a first portion of the wastes, and the green algae assimilate the remaining portion of the wastes to produce a substantially purified effluent stream. Haerther et al. discloses a system and method provided for aerobic treatment of waste, which includes the continual introduction of microalgae. The high amounts of oxygen produced by the microalgae satisfy the BOD in the treatment process and also allow oxidation of undesirable contaminants. These known systems and methods using algae undesirably require photosynthesis in order to grow the algae and treat the wastewater.

Another algal-based system and method for wastewater treatment is described by Nakajima et al. in *A Photo-Bioreactor using Algal Phototaxis for Solids-Liquid Separation*, Wat. Res. Vol. 25, No. 10, pp. 1243-1247, 1991, the entire disclosure of which is hereby incorporated herein by reference. Nakajima et al. uses the positive phototaxis characteristics of *Euglena gracilis* to separate the algal biomass from wastewater, following removal of nutritive substances from the wastewater by the *Euglena gracilis*.

Generating renewable biomass in wastewater using such methods is difficult. Specifically, most algae require abundant natural light in order to drive photosynthesis and grow the biomass. It is also difficult to limit an algae population to a single species of algae, and prevent other microorganisms from competing in the holding tanks or ponds. Separation of the biomass from an aqueous environment in which the biomass is grown is also difficult due to the generally small cell size of the aquatic organisms used for the wastewater treatment and relatively dilute concentrations of algae biomass (e.g. typically far less than 1% solids).

There is a continuing need for a system and method for treating high-strength wastewater having high BOO, and high nitrogen and phosphorus concentrations, which produces a valuable biomass by-product that can be used as a feedstock for ethanol production or other bioenergy production. There is a further need for a system and method that also optimizes microorganism biomass harvesting. Desirably, the system and method can be used as a pre-treatment for industrial wastewater producers or in municipal wastewater treatment plants to permanently remove BOD, nitrogen, and phosphorus from the wastewater stream.

SUMMARY OF THE INVENTION

In concordance with the instant disclosure a system and method for treating high-strength wastewater having high biological oxygen demand (BOD), and high nitrogen and phosphorus concentrations, which produces a valuable biomass by-product that can be used as a feedstock for ethanol production or other bioenergy production, that also optimizes microorganism biomass harvesting, and which can be used as a pre-treatment for industrial wastewater producers or in municipal wastewater treatment plants to permanently remove BOO, nitrogen, and phosphorus from the wastewater stream, is surprisingly discovered.

In an exemplary embodiment, the system and method of the present disclosure solves at least two problems known in the art of wastewater treatment. First, producing algae as a biomass feedstock is hampered by extremely high capital and operating costs. Most of this is due to the fact that algal ponds or bioreactors have relatively dilute biomass concentrations because algae are usually dependent on sunlight for growth. This makes harvesting the biomass harder via centrifuges or other processes very energy intensive. The second problem is that current wastewater treatment plants are utilizing bacteria to reduce nutrient and BOD concentrations. In some cases, not all of the nutrients, especially nitrogen and phosphorus, are removed from the water and extra steps are needed to remove the remaining nutrients.

The present wastewater treatment system and method utilizes a bioreactor with a population of heterotrophic microorganisms that exhibit a negative phototactic response, in place of the conventional bacteria. The phototactic heterotrophic microorganisms remove the nutrients and convert the organic carbon found in wastewater into a higher-value biomass that can be further processed into products such as biofuels, bioenergy, bioplastics, biofertilizers, animal feed and nutritional/pharmaceutical ingredients. The phototactic heterotrophic microorganisms grow heterotrophically on the organic carbon in the wastewater and are not dependent on sunlight for growth, which allows a much higher biomass density to accumulate in the bioreactor. The phototactic heterotrophic microorganisms may or may not also grow photosynthetically when exposed to sufficient light but they have the capability of growing heterotrophically in nutrient-laden conditions. The increased biomass density also permits a much higher efficiency in harvesting a biomass formed from the phototactic heterotrophic microorganisms.

Not every type of phototactic heterotrophic microorganism is well suited for growing in high nutrient environments. However, some species including Euglenoids grow very well and are commonly found in highly polluted areas. Euglenoids are a group of protists most similar to algae, but have several inherent differences that make their use particularly advantageous for a combined wastewater and biofuel production process.

One of the advantages of Euglenoids is that they are able to grow heterotrophically, and at faster rates than through autotrophic (photosynthetic) growth, on a wide variety of organic carbon substrates including alcohols and simple sugars. On a surface area basis, heterotrophic microorganism growth can conservatively achieve several times higher biomass yields than would be possible using sunlight alone. Additionally, Euglenoids produce a unique carbon storage product known as "paramylon", which is similar to a starch. This carbon storage product can account for more than seventy percent (70%) of the dry biomass of a cell, making Euglenoids an attractive organism for growing in mass quantities for the production of carbohydrates that can be converted into biofuels, bioenergy, bioplastics, and nutritional/pharmaceutical ingredients. The paramylon storage product can be isolated very easily by lysing the cells with a weak base solution (KOH, NaOH, etc.). Since the paramylon is much denser than the remaining cell material, the paramylon falls out of solution rapidly and facilitates the harvesting the paramylon.

Furthermore, Euglenoids are phototactic and can move towards (i.e., positive phototaxis) or away (i.e., negative phototaxis) from light. This results in a natural concentrating mechanism, which makes harvesting of the biomass even more efficient. The negative phototaxis characteristic of Euglenoids has not heretofore been employed for concentration and harvesting of Euglenoids.

The Euglenoid cells are grown in large, deep (>1 m), aerated basins or bioreactors. High strength wastewater, characterized by high BOD, high total nitrogen concentration, and high total phosphorus concentration, is added continuously to the bioreactor to supply nutrients and organic carbon substrate. For a brewery effluent scenario, a large amount of the BOD content (approximately 2000 mg BOD/liter) is composed of organic substrates that Euglenoids can consume. Up to about thirty percent (30%) of the consumable BOD is then converted into the Euglenoid biomass, the remaining BOD is respired. Nitrogen and phosphorus are similarly taken up into the Euglenoid biomass. In general, about 5-10 kg of nitrogen and about 0.5 to 2 kg of phosphorus are removed from the wastewater per 100 kg of Euglenoid biomass generated.

Based on BOD, nitrogen and phosphorus concentrations of brewery or ethanol distillery effluent (>2000 mg BOD/liter), Euglenoid biomass can easily reach 0.5 g/liter (as dry weight of cells), with a hydraulic retention time of around one to two days. The resulting liquid that is removed from the bioreactor then has a Euglenoid biomass density of about 0.5 g/liter, or approximately 0.05% solids. The dilute slurry needs to be concentrated to at least about twenty percent (20%) solids to be economically feasible for shipping the Euglenoid biomass to a facility for a higher-value biomass processing.

The initial concentration step for the Euglenoid biomass can be achieved in a variety of ways. In a first example, the dilute (0.05% solids) slurry is treated with a weak base (e.g., about 0.1 M NaOH or KOH) to lyse the Euglenoid cells. The treated slurry is then sent through an industrial scale clarifier, where dense solids fall out of suspension and clear effluent is discharged. Another alternative solution is to use the negative phototactic ability of *Euglena* to induce the cells to self concentrate. This could be achieved in a modified clarifier as well, where intense light is introduced at the top of the clarifier and cells are induced to swim away (downwards) from the light, thus achieving a similar goal as simply allowing the cells to settle by gravity alone or with chemical flocculation. A third alternative, although not a novel invention, is to use a non-chemical flocculent like Chitosan to induce rapid settling.

The initial concentration step results in a slurry that can approach 20 g/liter (i.e. 2% solids). At this concentration, centrifuging the slurry to twenty percent (20%) solids is not prohibitively capital intensive or energy intensive. The resulting twenty percent solids slurry, after centrifuging, resembles a thick paste and this Euglenoid biomass can be shipped economically to an offsite facility for processing into biofuels, bioenergy, bioplastics, biofertilizers, animal feed and nutritional/pharmaceutical ingredients. Paramylon can be chemically hydrolyzed into glucose and it is possible that this step could be completed prior to shipping to an ethanol distillery depending on the feedstock needs of the plant.

In one embodiment, a wastewater treatment method includes the steps of: providing an aerated bioreactor supporting a population of a phototactic heterotrophic microorganism; supplying a wastewater influent having nutrients and organic carbon substrate for the phototactic heterotrophic microorganism population to the aerated bioreactor; converting at least a portion of the nutrients and organic carbon substrate into the phototactic heterotrophic microorganism population, the wastewater influent and the phototactic heterotrophic microorganism together forming a bioreactor effluent; transferring the bioreactor effluent from the bioreactor to a light clarifier; concentrating the bioreactor effluent in the light clarifier to form a low-solids effluent and a high-solids effluent, the concentration performed by inducing the phototactic heterotrophic microorganism population to phototactically self concentrate by exposing the phototactic heterotrophic microorganism population to a light having at least one of an intensity and a wavelength sufficient to cause the phototactic heterotrophic microorganism population to migrate away from the light, wherein the phototactic heterotrophic microorganism population is concentrated to form the high-solids effluent and leave the low-solids effluent; dewatering the high-solids effluent to form a concentrated biomass paste; and processing the low-solids effluent to form a treated water stream.

In another embodiment, a system for treating wastewater includes an aerated bioreactor and a light clarifier. The aerated bioreactor supports a population of a phototactic heterotrophic microorganism. The aerated bioreactor is configured to receive a wastewater influent having nutrients and organic carbon substrate for the phototactic heterotrophic microorganism population. The wastewater influent and the phototactic heterotrophic microorganism population together form a bioreactor effluent. The light clarifier is in fluid communication with the aerated bioreactor. The light clarifier is configured to receive the bioreactor effluent and expose the phototactic heterotrophic microorganism population to a light having at least one of an intensity and a wavelength sufficient to cause the phototactic heterotrophic microorganism population to migrate away from a source of the light. The phototactic heterotrophic microorganism population is concentrated to form a high-solids effluent and leave a low-solids effluent.

In a further embodiment, a biomass cultivation method includes the steps of: providing an aerated bioreactor supporting a population of a phototactic heterotrophic microorganism; supplying a influent stream having nutrients and organic carbon substrate for the phototactic heterotrophic microorganism population to the aerated bioreactor; converting at least a portion of the nutrients and organic carbon substrate into the phototactic heterotrophic microorganism population, the influent stream and the phototactic heterotrophic microorganism together forming a bioreactor effluent; transferring the bioreactor effluent from the bioreactor to a light clarifier; concentrating the bioreactor effluent in the light clarifier to form a low-solids effluent and a high-solids effluent, the concentration performed by inducing the phototactic heterotrophic microorganism population to phototactically self concentrate by exposing the phototactic heterotrophic microorganism population to a light having at least one of an intensity and a wavelength sufficient to cause the phototactic heterotrophic microorganism population to migrate away from the light, wherein the phototactic heterotrophic microorganism population is concentrated to form the high-solids effluent and leave the low-solids effluent; and at least one of dewatering and drying the high-solids effluent to form a concentrated biomass paste.

In a different embodiment, the heterotrophic microorganism is grown photosynthetically during periods of sunlight and then is grown heterotrophically during periods of darkness. The purpose of this embodiment is to reduce the overall energy and carbon source required by the system without sacrificing the ability of the system to achieve high levels of treatment of BOD, nitrogen, or phosphorus.

In an additional embodiment, the heterotrophic microorganism may be grown for the removal of any chemical element or compound that is capable of being absorbed by, broken down by, or bound to the heterotrophic microorganism. Such an embodiment may include the removal of undesirable metals, biological toxins, endocrine disrupting compounds, or for the recovery of a valuable metal.

In an alternative embodiment, some fraction of the high-solids effluent leaving the light clarifier is diverted back to the aerated bioreactor. The purpose of this embodiment is to supplement the bioreactors with a high concentration of the targeted heterotrophic organism in order to maintain the dominance of that organism in the bioreactor and increase the effective biomass of the organisms in the bioreactor in order to increase the uptake rate of the pollutants (BOD, N, P, etc.).

In a further embodiment, a membrane reactor can be used to increase the concentration of the heterotrophic organism in a liquid on one side of the membrane and produce a filtered effluent that passes through the membrane. This can be achieved by pressurizing the liquid that contains the organism cells against a membrane surface or applying a vacuum on the opposing side of the membrane to draw filtered water through the membrane surface.

In another embodiment, a set of bioreactors can be arranged in series so that effluent from one reactor flows into another. The purpose of this embodiment is to allow different operating conditions in each bioreactor and/or allow for enhanced treatment of the wastewater as the targeted pollutant is progressively reduced from each successive bioreactor.

In another embodiment, the bioreactor can also serve as a light clarifier. The purpose of this embodiment is to allow the organisms to grow under normal operating conditions (e.g. with aeration and mixing) and then switch to a clarifier mode by switching of the aeration and mixing. Under low turbulence conditions and with sufficient light intensity at the correct wavelengths, the phototactic cells will migrate to the bottom of the bioreactor, leaving a low solid liquid near the surface and a high solid liquid at the bottom. These two liquid fractions can then be pumped out of the tanks independently.

DRAWINGS

The above, as well as other advantages of the present disclosure, will become readily apparent to those skilled in the art from the following detailed description, particularly when considered in the light of the drawings described herein.

DETAILED DESCRIPTION OF THE INVENTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the order of the steps presented is exemplary in nature, and thus, is not necessary or critical.

Figure 1:
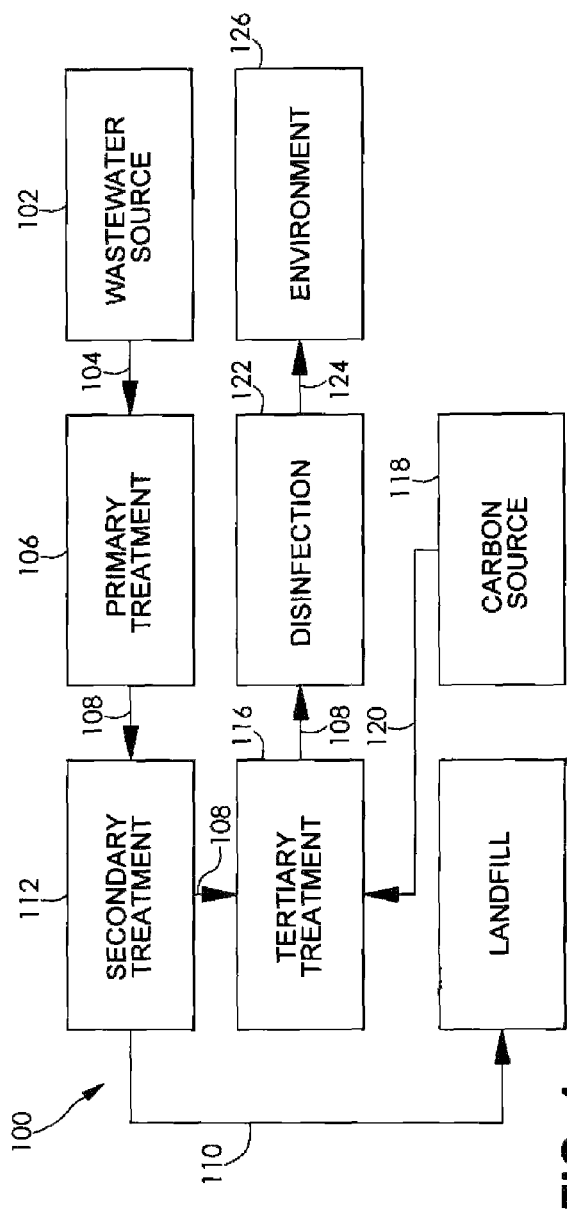
FIG. 1 is a flow diagram illustrating a prior art municipal wastewater treatment system and method.
Figure 2:
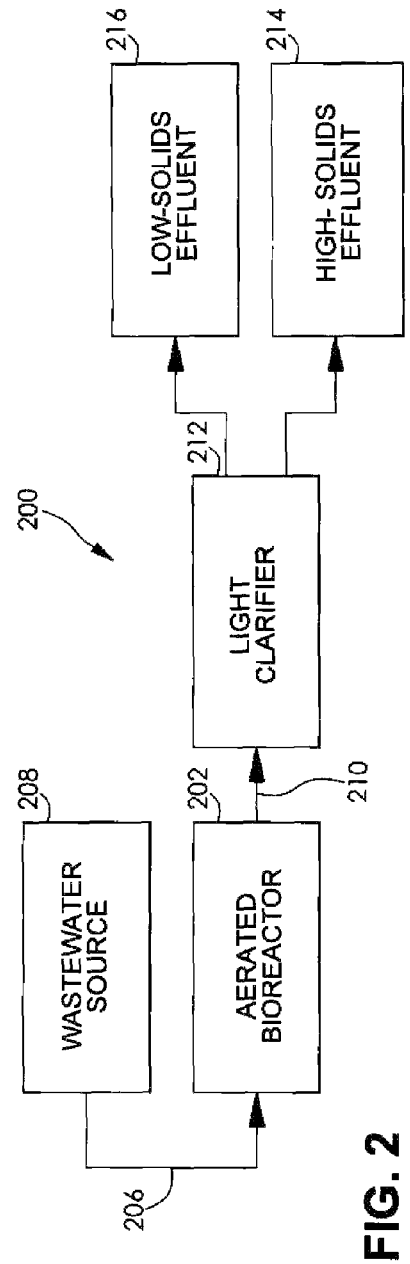
FIG. 2 is a flow diagram illustrating a wastewater treatment system and method according to one embodiment of the present disclosure.

As illustrated in FIG. 2, the present disclosure includes a wastewater treatment and biomass cultivation method 200. The method 200 includes the step of providing an aerated bioreactor 202. The aerated bioreactor 202 supports a population of a phototactic heterotrophic microorganism 204 (shown in FIG. 5). The phototactic heterotrophic microorganism population 204 includes at least one of a phototactic protist and a phototactic heterotrophic alga, for example. As one example, the phototactic heterotrophic microorganism 204 may include a photosynthetic and heterotrophic protozoan that, in the presence of excess organic carbon, grows primarily by organic carbon assimilation, i.e., a heterotrophic metabolism.

In one embodiment, the phototactic heterotrophic microorganism 204 is a Euglenoid, for example, from the genus *Euglena*. Euglenoids exhibit phototaxis in which the whole organism moves in response to an exposure to light. Many Euglenoids can glide and swim using their flagella, or can ooze along a substrate with an undulating, shape-changing, contraction motion called metaboly. The genus *Euglena* is a photosynthetic Euglenoid that includes over one hundred and fifty (150) known species. In an illustrative embodiment, the phototactic heterotrophic microorganism 204 employed in the system and method 200 is *Euglena gracilis*.

It should be understood that the phototactic heterotrophic microorganism 204 which is selected for the present system and method 200 exhibits negative phototaxis upon exposure to light of at least one of a sufficient intensity and a sufficient wavelength. For example, the phototactic heterotrophic microorganism 204 is a Euglenoid as described hereinabove. It should be appreciated that other types of the phototactic heterotrophic microorganism 204 exhibiting negative phototaxis upon exposure to the light of the sufficient intensity may also be employed within the scope of the present disclosure. A skilled artisan should further appreciate that the use of the negative phototactic response, as opposed to the use of the positive phototactic response as known in the art, advantageously permits a forced concentration and sedimentation of the phototactic heterotrophic microorganism population 204, as desired.

A wastewater influent 206 having nutrients and organic carbon substrate for the phototactic heterotrophic microorganism population 204 is supplied to the aerated bioreactor 202 from a wastewater source 208. It should be understood that the system and method 200 of the present disclosure may be employed with a variety of wastewater sources 208. As nonlimiting examples, the wastewater source 208 may include at least one of a municipal sewer line, a brewery, a distillery, a creamery, a chicken and/or egg farm, and a food or beverage manufacturer. Other wastewater sources 208 providing the wastewater influent 206 with sufficient nutrients and carbon substrate for the phototactic heterotrophic microorganism population 204 may also be employed, as desired. In a particular example, the wastewater influent 206 has a BOD and high nitrogen and phosphorus concentrations sufficient to promote a heterotrophic growth of the phototactic heterotrophic microorganism population 204 in the aerated bioreactor 202. Additionally, although the present method 200 is described primary with respect to wastewater influent 206 from the wastewater source 208, it should be understood that any suitable influent stream 206 having nutrients and organic carbon substrate sufficient to sustain the phototactic heterotrophic microorganism population 204, may also be employed is desired.

At least a portion of the nutrients and the carbon substrate is converted into the phototactic heterotrophic microorganism population 204 via the heterotrophic growth in the aerated bioreactor 202. The wastewater influent 206 and the phototactic heterotrophic microorganism population 204 together form a bioreactor effluent 210. For example, the wastewater influent 206 and the phototactic heterotrophic microorganism population 204 may be gently mixed in the bioreactor 202 to form the bioreactor effluent 210 having a generally homogenous consistency. The mixing is conducted without causing significant damage to the phototactic heterotrophic microorganism population 204.

Where the phototactic heterotrophic microorganisms 204 have chloroplasts that enable the phototactic heterotrophic microorganisms 204 to photosynthesize, such as where the phototactic heterotrophic microorganisms 204 are Euglenoids, the present method 200 may include the step of exposing the phototactic heterotrophic microorganisms 204 to a light having an intensity sufficient to promote a growth within the aerated bioreactor 202. The light promoting the growth of the phototactic heterotrophic microorganisms 204 may be provided by natural sunlight, for example. In an exemplary embodiment, the light promoting the growth of the phototactic heterotrophic microorganisms 204 may be artificial light produced at wavelengths from about 560 to about 810, particularly from about 585 to about 775, and most particularly from about 610 nm to about 760 nm. Other wavelengths of artificial light may also be used.

The bioreactor effluent 210 is transferred from the bioreactor 202 to a light clarifier 212. The bioreactor effluent 202 is concentrated in the light clarifier 212 to form a high-solids effluent 214 and a low-solids effluent 216. Advantageously, the concentration is performed by inducing the phototactic heterotrophic microorganism population 204 to phototactically self concentrate through exposure of the phototactic heterotrophic microorganism population 204 to light having at least one of a sufficient intensity and a sufficient wavelength. The light causes the phototactic heterotrophic microorganisms 204 to migrate away from a source 218 (shown in FIG. 6) of the light. The phototactic heterotrophic microorganism population 204 is thereby concentrated to form the high-solids effluent 214, and separated from the low-solids effluent 216.

The step of transferring the bioreactor effluent 210 may be conducted, for example, when a sensor network (not shown)

for detecting a nutrient content of the bioreactor effluent 210 reveals that the nutrient content has reached a predetermined minimum value. The predetermined minimum value may be one associated with little or no additional growth potential for the phototactic heterotrophic microorganism population 204 in the bioreactor effluent 210. A computer system (not shown) in electrical communication with the sensor network may provide a closed-loop information feedback system that monitors the BOD, nitrogen, and phosphorous levels of the bioreactor effluent 210. Alternatively, the sensor network monitors a ratio of BOD:nitrogen:phosphorus in the bioreactor effluent 210. The sensor network may also be employed to select when the bioreactor 202 should be re-seeded with a first portion 226 of the high-solids effluent 214, as desired.

In certain embodiments, the light to which the phototactic heterotrophic microorganism population 204 is exposed to cause the self concentration has a wavelength limited to a range that causes a negative phototactic response in the phototactic heterotrophic microorganism population 204. It has been found that the light having the wavelength from about 400 nm to about 550 nm, and particularly from about 425 nm to about 525 nm, and most particularly from 450 nm to about 500 nm, is surprisingly effective for causing the negative phototactic response of Euglenoids. Exposure to light having wavelengths limited to these ranges may provide a superior negative phototactic response of Euglenoids in comparison to fluorescent or halogen lighting having a broad spectrum of wavelengths. Other suitable wavelengths and intensities of the light adapted to cause the self concentration may be selected as desired, for example, based on the species of the phototactic heterotrophic microorganism population 204 chosen for the system and method 200.

Figure 3:
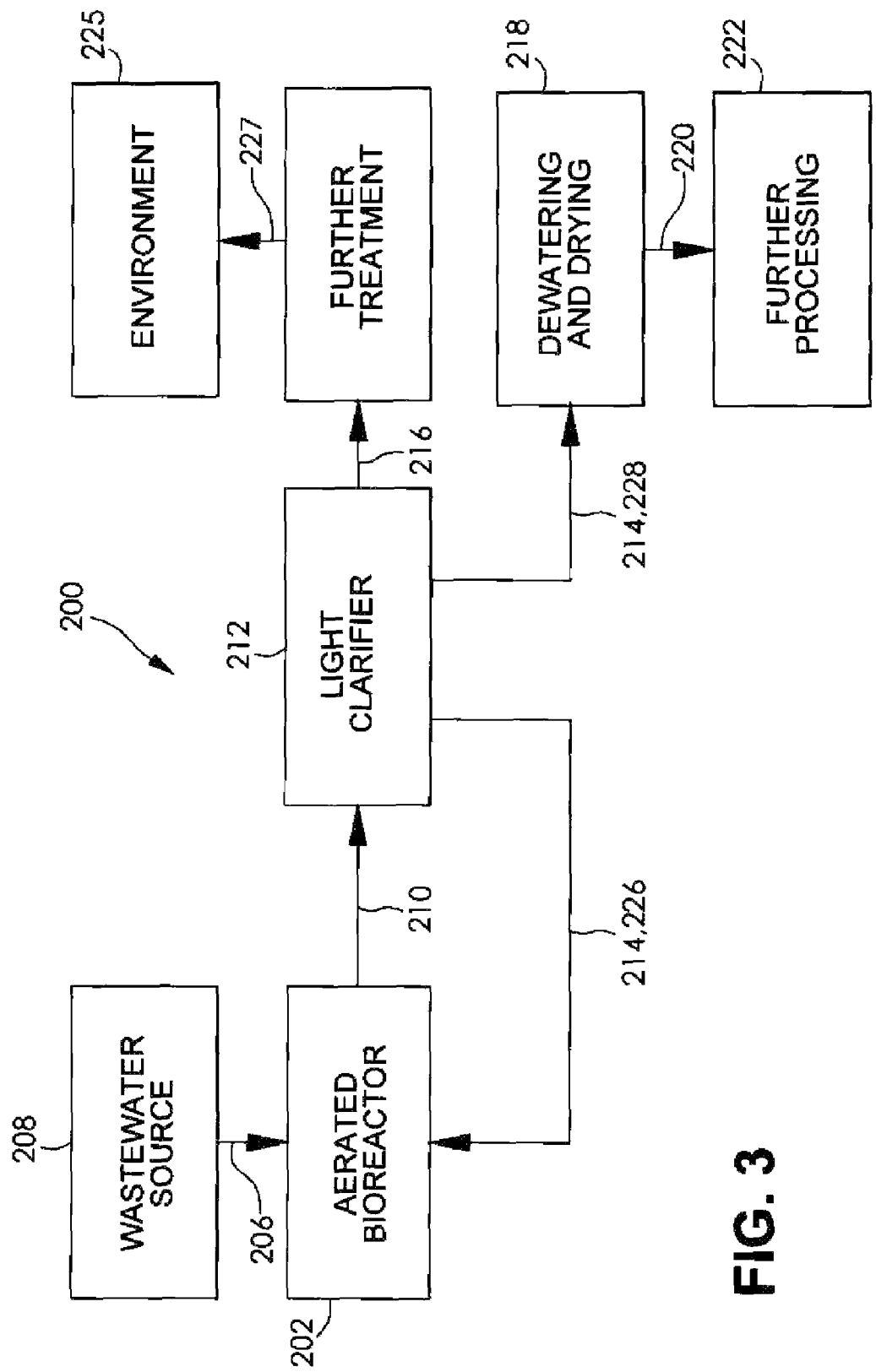
FIG. 3 is a flow diagram illustrating a wastewater treatment system and method according to another embodiment of the present disclosure.

In a particular embodiment shown in FIG. 3, the method 200 may include further processing steps following the formation of the high-solids effluent 214 and the low-solids effluent 216. For example, the high-solids effluent 214 may undergo at least one of a dewatering 218 and a drying to form a concentrated biomass paste 220. As nonlimiting examples, the step of dewatering the high-solids effluent 214 includes one of centrifuging, belt pressing, and heated screw pressing the high-solids effluent 214 until the biomass paste 220 having a desired concentration is formed. In a particularly illustrative example, the desired concentration may be up to about twenty percent (20%) solids by weight of the high-solids effluent 214. A skilled artisan may select other desired concentrations of the biomass paste 220, as desired.

The concentrated biomass paste 220 may then be transported and undergo further processing 222. It should be appreciated that the further processing may include the steps of hydrolyzing the biomass paste 220, and converting the hydrolyzed biomass paste 220 into ethanol, for example, using conventional fermentation techniques. Alternatively, the concentrated biomass paste 220 may be employed as a fertilizer or soil conditioner, or animal feed, or for co-firing at a power plant, or in an anaerobic digestor or other bioenergy uses. Additionally, the biomass can be utilized in the production bioplastics, or nutritional/pharmaceutical ingredients. Other suitable end uses for the concentrated biomass paste 220 are also within the scope of the present disclosure.

As shown in FIG. 3, the wastewater treatment method 200 further includes the steps of diverting a first portion 226 of the high-solids effluent 214 to the bioreactor 202, and dewatering a second portion 228 of the high-solids effluent 214 to provide the concentrated biomass paste 220. The diverting of the first portion 226 of the high-solids effluent 214 to the bioreactor 202 causes a re-seeding of the bioreactor 202, and encourages further growth of the phototactic heterotrophic microorganism population 204 therein. The re-seeding of the bioreactor 202 may be conducted as part of a batch process for production of the biomass paste 220. In an alternative embodiment, the first portion 226 may also be dewatered instead of re-seeding the bioreactor 202, thereby providing for a continuous production process for the biomass paste 220.

With renewed reference to FIG. 2, it should be appreciated that the bioreactor effluent 210 may also undergo an additional treatment. The additional treatment of the bioreactor effluent 210 may include at least one of a filtering step and a disinfection step, as nonlimiting examples. Other additional treatments may also be used, as desired. In one example, the additional treatment of the bioreactor effluent 210 includes the step of treating the bioreactor effluent 210 with a base to lyse at least a fraction of the heterotrophic microorganism population 204 in the bioreactor effluent 210. The treated bioreactor effluent 210 may then be directed through a secondary clarifier (not shown) for precipitation of the lysed fraction of the heterotrophic microorganism population 204. In another example, a flocculent is added to the bioreactor effluent 210. The flocculent may be any conventional flocculent such as Chitosan and the like. The flocculent induces a rapid settling of the heterotrophic microorganism population and produces a high-solids bottom layer and low-solids top layer in a standard gravity clarifier. In an additional example, the additional treatment of the bioreactor effluent 216 includes the step of filtering the bioreactor effluent 210 through a membrane filter (not shown) to remove the at least a fraction of the phototactic heterotrophic microorganism population 204 in the bioreactor effluent 210. A membrane clarifier can be used during the membrane filtration to increase the concentration of the heterotrophic microorganism population 204 in a liquid on one side of the membrane and produce a filtered effluent that passes through the membrane. This can be achieved by pressurizing the liquid that contains the microorganism cells against a membrane surface or applying a vacuum on the opposing side of the membrane to draw filtered water through the membrane surface.

Figure 4:
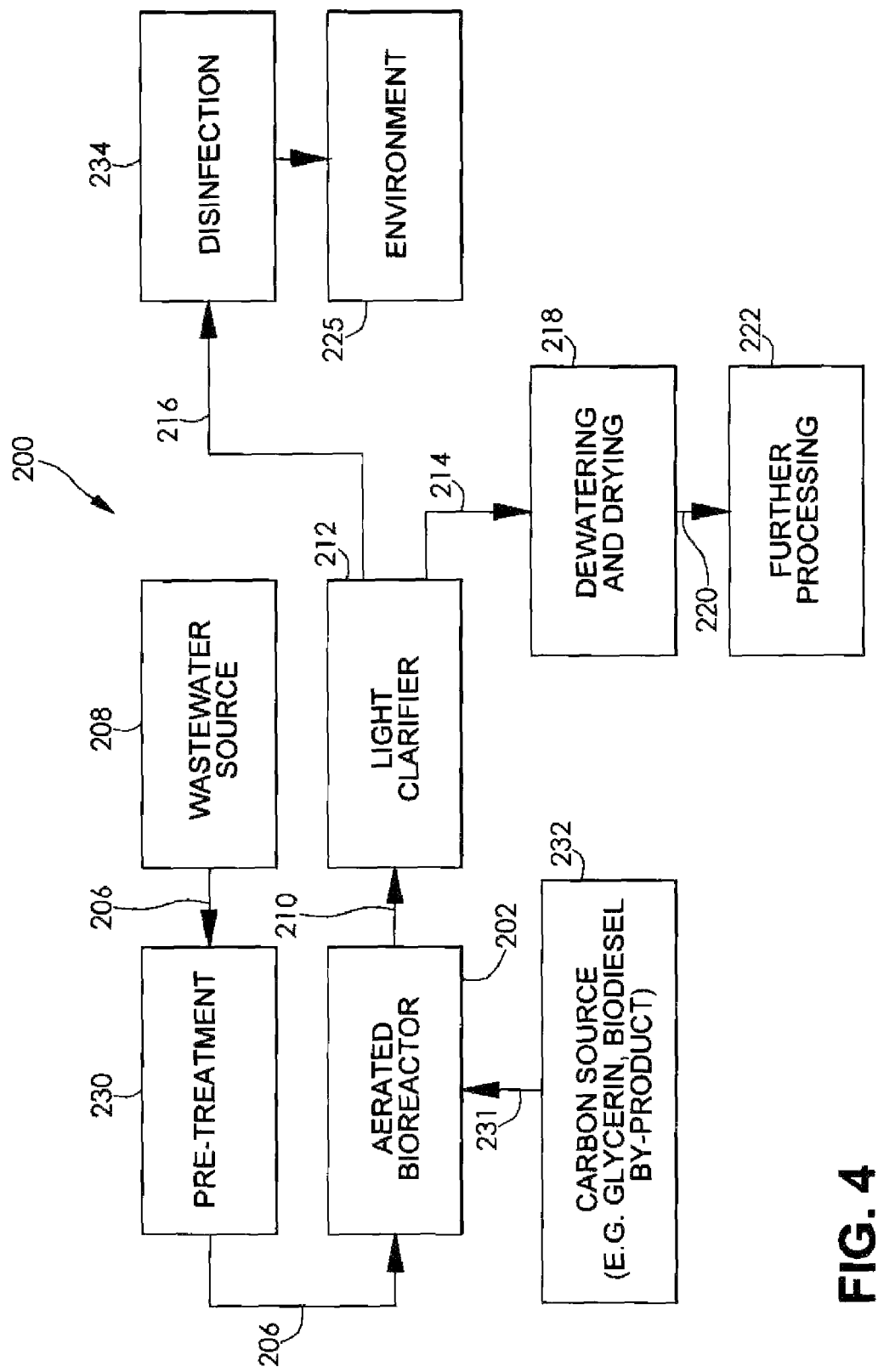
FIG. 4 is a flow diagram illustrating a wastewater treatment system and method according to a further embodiment of the present disclosure.

In an alternative embodiment shown in FIG. 4, the method 200 adapted for use in an industrial or municipal wastewater treatment is illustrated. The wastewater influent 206 may undergo at least one of a pre-treatment 230 including screening for removal of large objects and waste carried in the wastewater influent 206. Additionally, the wastewater influent 206 may be supplemented with a supplemental stream 231 including at least one of nutrients and organic carbon substrate, for example, from a secondary carbon source 232. The secondary carbon source 232 is advantageously a low commercial value carbon source 232. As nonlimiting examples, the secondary carbon source 232 may include at least one of glycerin and a biodiesel by-product. Other waste or low commercial value streams for the secondary carbon source 232 may also be employed, as desired.

Following the separation of the high-solids effluent 214 from the low-solids effluent 216 in the light clarifier 212, the low-solids effluent 216 may undergo a disinfection treatment 234. The purpose of the disinfection treatment 234 is to substantially reduce the quantity of phototactic heterotrophic microorganisms 204 such as the Euglenoids to be discharged back into the environment 225, for example, to a river. In particular embodiments, the disinfection treatment 234 includes exposing the low-solids effluent 216 to at least one of ozone, chlorine, ultraviolet light, or sodium hypochlorite, although other suitable forms for reducing the quantity of phototactic heterotrophic microorganisms 204 discharged to the environment 225 may also be used.

In a further embodiment according to the present disclosure, the wastewater treatment method 200 includes the step of fractionating the concentrated biomass paste 220. As non-limiting examples, the concentrated biomass paste 220 is fractionated by at least one of acid fractionation, base fractionation, high pressure fractionation, for example, by a rapid non-equilibrium decompression of the concentrated biomass paste 220, and mechanical fractionation. Where the phototactic heterotrophic microorganism population 204 includes Euglenoids, the fractionation may form a paramylon fraction and a non-paramylon fraction. Paramylon is a β-1,3 polymer of glucose with certain similarities to a starch. Paramylon is found as rod like bodies through the cytoplasm of Euglenoids. The paramylon may be particularly useful for the manufacturing of bio-plastics, and for certain medicinal applications known in the art.

The paramylon from the phototactic heterotrophic microorganism population 204 may be chemically hydrolyzed into glucose, for example, prior to shipping the glucose to a distillery for purpose of fermentation and ethanol production. The non-paramylon fraction is generally nitrogen and phosphorus enriched, and thereby may be suitable as a fertilizer or in certain animal feeds. The non-paramylon fraction resulting from the fractionation of the phototactic heterotrophic microorganism population 204 may also include a wax-ester fraction of commercial value. It should be appreciated that the wax-ester fraction may be greater at higher fractionation temperatures, and under more anaerobic conditions.

One of ordinary skill in the art should appreciate that the phototactic heterotrophic microorganisms 204 such as Euglenoids may be effectively cultivated at a pH that favors growth of the phototactic heterotrophic microorganism population 204, while militating against growth of competitor microorganisms such as bacteria, protozoa, chlorophytes, and fungi. The effects of pH on growth of phototactic heterotrophic microorganisms 204 is described by Waygood et al, in *Purification and Reclamation of Farm and Urban Wastes by Euglena Gracilis: Photosynthetic Capacity, Effect of pH, Temperature, Acetate and Whey*, Environmental Pollution (Series A) 23 (1980) 179-215, the entire disclosure of which is hereby incorporated herein by reference.

The wastewater treatment method 200 may include the further step of adjusting the pH of the bioreactor effluent 210 in order to favor the phototactic heterotrophic microorganism population 204 over the competitor microorganisms. The pH of the bioreactor effluent 210 may be adjusted by adding an acid such as acetic acid, or a base such as sodium hydroxide. Other acids and bases, for example, also providing nutritive value to the bioreactor effluent 210, may also be employed. In certain embodiments, the pH of the bioreactor effluent 210 may be lowered to less than about pH=4.0, particularly to less than about pH=3.6, and most particularly to about pH=3.2. The pH of the bioreactor effluent 210 may be adjusted to other levels sufficient to militate against growth of competitor microorganisms, as desired.

The pH of the bioreactor effluent 210 may also be adjusted to increase the growth of filament forming organisms other than the phototactic heterotrophic microorganism population 204 such as fungi, for example, following depletion of the nutrients from the bioreactor effluent 210 by the phototactic heterotrophic microorganism population 204. It should be appreciated that the growth of filament forming organisms in addition to the phototactic heterotrophic microorganism population 204 may advantageously facilitate the harvesting of the high-solids effluent 214 and the concentrated biomass paste 220.

Although the method 200 detailed hereinabove has been described with respect to wastewater treatment, it should be understood that the method 200 may also be used primarily for cultivation of the concentrated biomass paste 220. For example, an illustrative biomass cultivation method may comprise the steps of: providing the aerated bioreactor 202 supporting the population of a phototactic heterotrophic microorganism 204; supplying to the aerated bioreactor 202 an influent stream, for example, the wastewater stream 206, having nutrients and the organic carbon substrate for the phototactic heterotrophic microorganism population 204; and cultivating the phototactic heterotrophic microorganism population 204 to convert at least a portion of the nutrients and organic carbon substrate into the phototactic heterotrophic microorganism population 204, the influent stream 206 and the phototactic heterotrophic microorganism population 204 together forming the bioreactor effluent 210.

The biomass cultivation method further includes the step of concentrating the bioreactor effluent 210. The bioreactor effluent 210 may be concentrated with the light clarifier 212, as described hereinabove. In further embodiments, however, the bioreactor effluent 210 may alternatively be concentrated by treating the bioreactor effluent with a base to form the low-solids effluent 216 and the high-solids effluent 214. The base lyses at least a portion of the heterotrophic microorganism population 204 in the bioreactor effluent 210, which portion of the heterotrophic microorganism population 204 then precipitates to form the high-solids effluent 214.

The bioreactor effluent 210 may be concentrated through introduction of a flocculent to the bioreactor effluent 210. The flocculent induces a rapid settling of at least a portion of the heterotrophic microorganism population 204 to form the low-solids effluent 216 and the high-solids effluent 214.

In a particularly illustrative embodiment, the concentration of the bioreactor effluent 210 is performed by filtering the bioreactor effluent 210 through a water-permeable membrane filter (not shown) to remove at least a portion of the phototactic heterotrophic microorganism population 204 to form the low-solids effluent 214 and the high-solids effluent 216. The membrane is configured to permit water to pass therethrough, while filtering out microorganisms such as protists and algae. A membrane filtration system can be used to separate the solids (including the heterotrophic microorganism population 204) and liquid in the bioreactor effluent 210. The membrane filtration process increases the concentration of the heterotrophic microorganism population 204 in a liquid on one side of the membrane to become the high-solids effluent 216, and simultaneously produces a filtered effluent liquid that passes through the membrane to become the low-solids effluent 214. The membrane filtration can be achieved by pressurizing the bioreactor effluent 210 that contains the heterotrophic microorganism population 204 against the membrane surface, or by applying a vacuum on the opposing side of the membrane to draw filtered water through the membrane surface. This embodiment may include elements of the previously stated embodiments.

In another illustrative embodiment, the bioreactor effluent 210 may be separated into the low-solids effluent 214 and the high-solids effluent 216 by dissolved air flotation. In dissolved air flotation, small bubbles are formed from either compressed air, or another suitable process to form the small bubbles, in a liquid storage vessel. As the bubbles rise to the liquid's surface, they attach to particles, including the heterotrophic microorganism population 204 and generate a floating biomass floc. As more of the biomass becomes attached to the bubbles and rise to the surface, the underlying liquid is subsequently reduced in suspended solids.

Figure 5:
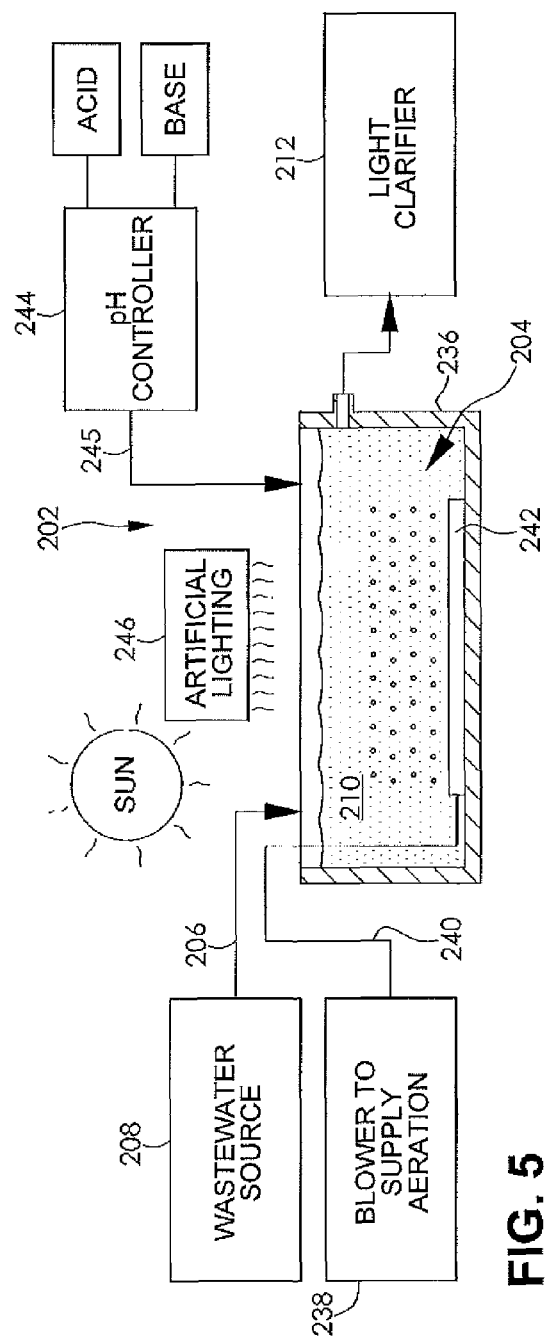
FIG. 5 is a schematic side cross-sectional elevational view of an exemplary bioreactor for use in the wastewater treatment systems and methods illustrated in FIGS. 2-4.

With reference to FIG. 5, an illustrative aerated bioreactor 202 for use with the method 200 of the present disclosure is shown. The bioreactor 202 may include a holding tank 236. The holding tank 236 may also be an open-air reservoir or a pond, as nonlimiting examples. The bioreactor 202 supports the population of the phototactic heterotrophic microorganism 204 and is configured to receive the wastewater influent 206 having nutrients and organic carbon substrate for the phototactic heterotrophic microorganism population 204. The wastewater influent 206 and the phototactic heterotrophic microorganism population 204 together form the bioreactor effluent 210 held in the bioreactor 202.

The bioreactor 202 may include mechanical mixers configured to provide a substantially uniform distribution of the phototactic heterotrophic microorganism population 204 throughout the holding tank 236. The bioreactor 202 may also be in communication with a blower 238 configured to aerate or oxygenate the bioreactor 202 by supplying an air stream 240 thereto. The air stream 240 may percolate up through the bioreactor effluent 210 from a series of perforated pipes 242 disposed at a base of the open holding tank 236. Other suitable means for aerating the bioreactor effluent 210 may also be employed.

The bioreactor 202 may also be in fluid communication with a pH controller 244. The pH controller 244 is configured to modulate or adjust the pH of the bioreactor effluent 210 in the bioreactor 202 by delivering a pH control stream 245 including at least one of an acid and a base thereto. The pH of the bioreactor effluent 204 is controlled within a range conducive for growth of the population of the phototactic heterotrophic microorganism 204, while militating against growth of competitor microorganisms.

An artificial light source 246 may be disposed above the holding tank 236 that forms the aerated bioreactor 202. The artificial light source 246 may be configured to generate the light having the intensity and wavelength sufficient to promote the growth of the phototactic heterotrophic microorganism population 204, while not causing the phototactic heterotrophic microorganism population 204 to self concentrate in the aerated bioreactor 202. For example, the artificial light source 246 may include a plurality of low power LED lights providing the desired range of light intensity and wavelength. Where the aerated bioreactor 202 is open to the atmosphere, the aerated bioreactor 202 may also be exposed to natural sunlight as shown in FIG. 5.

Figure 6:
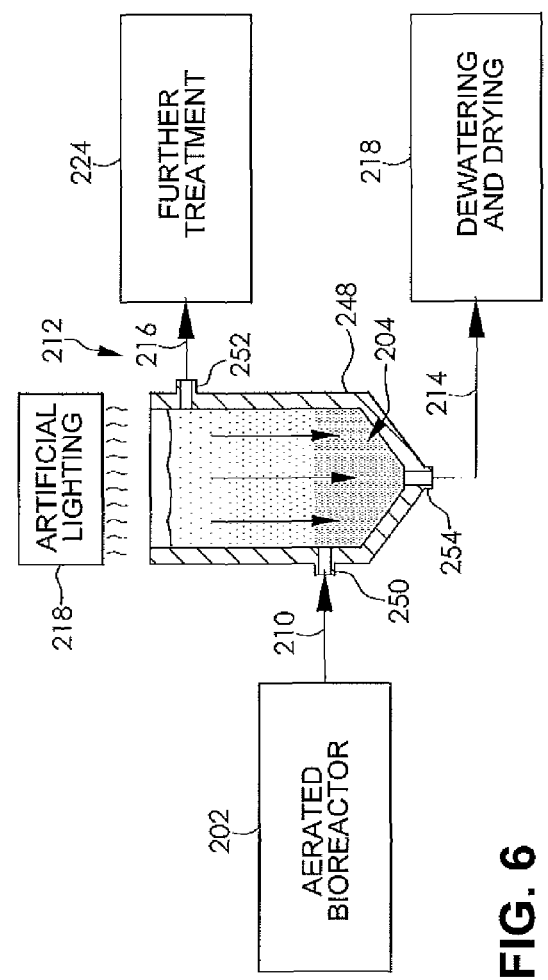
FIG. 6 is a schematic side cross-sectional elevational view of an exemplary light clarifier for use in the wastewater treatment systems and methods illustrated in FIGS. 2-4.

With reference to FIG. 6, an illustrative light clarifier 212 for use with the method 200 of the present disclosure is shown. The light clarifier 212 is in fluid communication with the aerated bioreactor 202. The light clarifier 212 is configured to receive the bioreactor effluent 210 and expose the phototactic heterotrophic microorganisms 204 to the light having at least one of a sufficient intensity and a sufficient wavelength to cause the phototactic heterotrophic microorganism population 204 to migrate away from the source 218 of the light.

The light clarifier 212 may include a holding vessel 248 having an inlet 250, a first outlet 252, and a second outlet 254. The holding vessel 248 may have a length greater than a width of the holding vessel 248. The greater length of the holding tank 248 may facilitate a phototactic sedimentation of the phototactic heterotrophic microorganism population 204 aided by gravity. The inlet 250 is in fluid communication with the bioreactor 202. The first outlet 252 is disposed near a top of the holding vessel 248 and permits the low-solids effluent 216 to flow therefrom after separation from the high solids effluent 214 inside of the light clarifier 212. The second outlet 254 is disposed near a bottom of the holding vessel 248 and permits the high-solids effluent 214 to flow therefrom after the separation in the light clarifier 212. The bottom of the holding vessel 248 may be substantially cone-shaped, or V-shaped in cross-section, and thereby shaped to facilitate the concentration of the phototactic heterotrophic microorganisms 204 near the second outlet 254.

The system of the present invention may include one or more other biomass concentrating subsystems (not shown) in addition to, or as alternatives to, the light clarifier 212 described herein. The biomass concentrating subsystem may include at least one of a lysing subsystem, a flocculation subsystem, a membrane filtration subsystem, and a dissolved air flotation subsystem. The at least one biomass concentrating subsystem is configured to separate solids, including the heterotrophic microorganism population 204, and liquid from the bioreactor effluent 210 to form the high-solids effluent 214 and the low-solids effluent 216, respectively.

Advantageously, the present wastewater treatment and biomass cultivating system and method 200 is suitable for treating high-strength wastewater influent 206 having high BOD and high nitrogen and phosphorus concentrations. The system and method 200 produces a valuable biomass 220 that can be used as a feedstock for ethanol production or other bioenergy production. The system and method 200 also optimizes microorganism biomass harvesting by taking advantage of the negative phototaxis characteristics of particular microorganisms. Negative phototaxis is a characteristic that was not heretofore appreciated or leveraged in the art with respect to wastewater treatment. The wastewater treatment and biomass cultivating system and method 200 can further be used as a pre-treatment for industrial wastewater producers, or in municipal wastewater treatment plants to permanently remove BOD, nitrogen and phosphorus from the wastewater influent 206.

While certain representative embodiments and details have been shown for purposes of illustrating the invention, it will be apparent to those skilled in the art that various changes may be made without departing from the scope of the disclosure, which is further described in the following appended claims.

What is claimed is:

1. A wastewater treatment and biomass cultivation method, the method comprising the steps of:
providing an aerated bioreactor supporting a population of a phototactic heterotrophic microorganism;
supplying to the aerated bioreactor a wastewater influent having nutrients and an organic carbon substrate for growth of the phototactic heterotrophic microorganism population;
cultivating the phototactic heterotrophic microorganism population to convert at least a portion of the nutrients and the organic carbon substrate into the phototactic heterotrophic microorganism population, the wastewater influent and the phototactic heterotrophic microorganism population together forming a bioreactor effluent;
transferring the bioreactor effluent from the bioreactor to a light clarifier;
concentrating the bioreactor effluent in the light clarifier to form a low-solids effluent and a high-solids effluent, the concentration performed by inducing the phototactic heterotrophic microorganism population to phototactically self concentrate by exposing the phototactic heterotrophic microorganism population to a source of light having at least one of an intensity and a wavelength sufficient to cause the phototactic heterotrophic microorganism population to migrate away from the source of light, wherein the phototactic heterotrophic microorganism population is concentrated to form the high-solids effluent;

dewatering the high-solids effluent to form a concentrated biomass paste; and processing the low-solids effluent to form a treated water stream.

2. The wastewater treatment method of claim 1, further comprising the steps of diverting a first portion of the high-solids effluent to the bioreactor and at least one of dewatering and drying a second portion of the high-solids effluent to provide a concentrated biomass paste.

3. The wastewater treatment method of claim 1, wherein the step of dewatering the high-solids effluent includes one of centrifuging, belt pressing, and heated screw pressing the high-solids effluent.

4. The wastewater treatment method of claim 1, further comprising the steps of hydrolyzing the biomass paste and converting the hydrolyzed paste into ethanol.

5. The wastewater treatment method of claim 1, wherein the phototactic heterotrophic microorganism is one of a phototactic protist and a phototactic alga exhibiting negative phototaxis.

6. The wastewater treatment method of claim 5, wherein the phototactic heterotrophic microorganism is a Euglenoid.

7. The wastewater treatment method of claim 1, wherein the wastewater influent includes a biological oxygen demand (BOD), a concentration of nitrogen, and a concentration of phosphorus sufficient to grow the phototactic heterotrophic microorganism population.

8. The wastewater treatment method of claim 1, wherein the wastewater influent is supplemented with a secondary carbon source including at least one of glycerin and a biodiesel by-product.

9. The wastewater treatment method of claim 1, wherein the biomass paste is fractionated by at least one of acid fractionation, base fractionation, high pressure fractionation, and mechanical fractionation to form a paramylon fraction and a non-paramylon fraction.

10. The wastewater treatment method of claim 9, wherein the non-paramylon fraction includes a wax-ester fraction.

11. The wastewater treatment method of claim 1, furthering including a step of adjusting a pH of the bioreactor effluent to favor growth of the phototactic heterotrophic microorganism population over growth of competitor microorganisms.

12. The wastewater treatment method of claim 1, wherein the source of light to which the phototactic heterotrophic microorganism population is exposed to cause the self concentration has a wavelength from about 400 nm to about 550 nm.

13. The wastewater treatment method of claim 1, wherein the phototactic heterotrophic microorganism is exposed to another source of light while in the aerated bioreactor, the another source of light having at least one of an intensity and a wavelength sufficient to promote a growth of the phototactic heterotrophic microorganism population.

14. A system for cultivating biomass, comprising:

an aerated bioreactor supporting a population of a phototactic heterotrophic microorganism and configured to receive an influent stream having nutrients and an organic carbon substrate for growth of the phototactic heterotrophic microorganism population, the influent stream and the phototactic heterotrophic microorganism population together forming a bioreactor effluent;

15. The system of claim 14, further comprising a light clarifier in fluid communication with the aerated bioreactor, the light clarifier configured to receive the bioreactor effluent and expose the phototactic heterotrophic microorganism population to a source of light having at least one of an intensity and a wavelength sufficient to cause the phototactic heterotrophic microorganism population to migrate away from the source of light, wherein the phototactic heterotrophic microorganism population is concentrated to form a high-solids effluent and leave a low-solids effluent.

16. The system of claim 15, wherein the source of light includes an artificial lighting system disposed adjacent the light clarifier and providing a light having at least one of an intensity and a wavelength sufficient to cause the phototactic heterotrophic microorganism population to self concentrate, and wherein the system further includes another artificial light system disposed adjacent the aerated bioreactor and providing another light having at least one of an intensity and a wavelength sufficient to promote a growth of the phototactic heterotrophic microorganism population and not cause the phototactic heterotrophic microorganism population to self concentrate in the aerated bioreactor.

17. The system of claim 14, further comprising a pH controller in fluid communication with the aerated bioreactor, the pH controller configured to modulate a pH of the bioreactor effluent, the modulated pH being conducive to growth of the population of the phototactic heterotrophic microorganism population and militating against growth of competitor microorganisms.

18. The system of claim 14, further comprising a biomass concentrating subsystem, the biomass concentrating subsystem including at least one of a lysing subsystem, a flocculation subsystem, a membrane filtration subsystem, and a dissolved air flotation subsystem to separate solids including the heterotrophic microorganism population and liquid from the bioreactor effluent.

19. A biomass cultivation method, the method comprising the steps of:

providing an aerated bioreactor supporting a population of a phototactic heterotrophic microorganism;

supplying to the aerated bioreactor an influent stream having nutrients and an organic carbon substrate for the phototactic heterotrophic microorganism population;

cultivating the phototactic heterotrophic microorganism population to convert at least a portion of the nutrients and organic carbon substrate into the phototactic heterotrophic microorganism population, the influent stream and the phototactic heterotrophic microorganism population together forming a bioreactor effluent; and at least one of concentrating the bioreactor effluent in the light clarifier to form a low-solids effluent and a high-solids effluent, the concentration performed by inducing the phototactic heterotrophic microorganism population to phototactically self concentrate by exposing the phototactic heterotrophic microorganism population to a source of light having at least one of an intensity and a wavelength sufficient to cause the phototactic heterotrophic microorganism population to migrate away from the source of light, wherein the phototactic heterotrophic microorganism population is concentrated to form the high-solids effluent, treating the bioreactor effluent with a base to form the low-solids effluent and the high-solids effluent, wherein the base lyses at least a portion of the heterotrophic microorganism population in the bioreactor effluent, and wherein the lysed heterotrophic microorganism population precipitates to form the high-solids effluent, introducing a flocculent to the bioreactor effluent to induce a rapid settling of at least a portion of the heterotrophic microorganism population to form the low-solids effluent and the high-solids effluent, filtering the bioreactor effluent through a membrane filter to remove at least a portion of the phototactic heterotrophic microorganism population to form the low-solids effluent and the high-solids effluent, and separating the bioreactor effluent into the low-solids effluent and the high-solids effluent by dissolved air flotation.

20. The biomass cultivation method of claim 19, further comprising the step of at least one of dewatering and drying the high-solids effluent to form a concentrated biomass paste.

* * * * *